(12) United States Patent
Inaba

(10) Patent No.: US 10,442,229 B2
(45) Date of Patent: Oct. 15, 2019

(54) INKJET RECORDING DEVICE AND TEST CHART DETECTION METHOD

(71) Applicant: KONICA MINOLTA, INC., Chiyoda-ku, Tokyo (JP)

(72) Inventor: Yasunori Inaba, Hino (JP)

(73) Assignee: Konica Minolta, Inc., Chiyoda-ku, Tokyo (JP)

( * ) Notice: Subject to any disclaimer, the term of this patent is extended or adjusted under 35 U.S.C. 154(b) by 0 days.

(21) Appl. No.: 16/034,616

(22) Filed: Jul. 13, 2018

(65) Prior Publication Data

US 2019/0023042 A1   Jan. 24, 2019

(30) Foreign Application Priority Data

Jul. 24, 2017   (JP) .................................. 2017-142451

(51) Int. Cl.
| | |
|---|---|
| B41J 29/393 | (2006.01) |
| B41J 2/21 | (2006.01) |
| B41J 2/01 | (2006.01) |
| G01N 21/64 | (2006.01) |
| B41J 2/165 | (2006.01) |
| G07B 17/00 | (2006.01) |

(52) U.S. Cl.
CPC .............. *B41J 29/393* (2013.01); *B41J 2/01* (2013.01); *B41J 2/2114* (2013.01); *B41J 2/2117* (2013.01); *B41J 2/2142* (2013.01); *G01N 21/64* (2013.01); *B41J 2/16579* (2013.01); *B41J 2029/3935* (2013.01); *G07B 2017/00653* (2013.01)

(58) Field of Classification Search
CPC .......... B41J 2/2135; B41J 29/393; B41J 2/01
USPC ........................................... 347/5, 19, 96, 98
See application file for complete search history.

(56) References Cited

U.S. PATENT DOCUMENTS

| | | | |
|---|---|---|---|
| 5,546,117 A | 8/1996 | Ohno et al. | |
| 6,378,976 B1 | 4/2002 | Byers et al. | |
| 2007/0206039 A1 | 9/2007 | Kawamura et al. | |
| 2008/0230719 A1 | 9/2008 | Pan et al. | |
| 2009/0237434 A1 | 9/2009 | Mantell et al. | |
| 2011/0249051 A1 | 10/2011 | Chrétien et al. | |

FOREIGN PATENT DOCUMENTS

| | | |
|---|---|---|
| EP | 2189291 A2 | 5/2010 |
| GB | 2391199 A | 2/2004 |
| JP | 2006-110804 A | 4/2006 |
| JP | 2017081008 A | 5/2017 |

OTHER PUBLICATIONS

The extended European Search Report dated Jan. 2, 2019, by the European Patent Office in corresponding European Application No. 18181392.4. (9 pages).

*Primary Examiner* — An H Do
(74) *Attorney, Agent, or Firm* — Buchanan Ingersoll & Rooney PC

(57) ABSTRACT

An inkjet recording device includes: an inkjet head that forms an image on a recording medium by ejecting ink containing a phosphor onto the recording medium; an ultraviolet light source that irradiates the image formed on the recording medium with ultraviolet rays; and an imager that detects fluorescence emitted by the image by the irradiation of the ultraviolet rays.

8 Claims, 8 Drawing Sheets

244

243 242

8, 8W, 8Y, 8M, 8C, 8Bk

INKJET RECORDING DEVICE AND TEST CHART DETECTION METHOD

The entire disclosure of Japanese patent Application No. 2017-142451, filed on Jul. 24, 2017, is incorporated herein by reference in its entirety.

BACKGROUND

Technological Field

The present invention relates to an inkjet recording device that forms an image by ejecting ink onto a recording medium and a test chart detection method in the inkjet recording device.

Description of the Related Art

In inkjet recording devices, an image is formed on a recording medium with ink ejected from nozzles of a recording head. In such inkjet recording devices, there are cases where a nozzle of a recording head is clogged and ejection failure of not ejecting ink occurs.

In order to detect such ejection failure, employed is a method of specifying a non-ejecting nozzle by causing nozzles of a recording head to eject ink, forming a predetermined test chart on a recording medium, and reading the test chart by an inline sensor.

Meanwhile, as for inks used in inkjet recording devices, white (W) ink and transparent ink that is used over another ink are known in addition to yellow (Y), magenta (M), cyan (C), and black (Bk). A transparent ink is used for the purpose of, for example, improving the light fastness or water resistance of an image or giving gloss to an image.

Since such white ink or transparent ink has poor visibility on a recording medium, there is a problem that when a test chart is formed, the test chart cannot be read by an inline sensor. Therefore, in the case where white ink or transparent ink is used, it is difficult to specify a non-ejecting nozzle by preparing a test chart and reading the test chart by an inline sensor.

To address this problem, JP 2006-110804 A discloses a method for detecting a test pattern "of detecting a test pattern by recording the test pattern on a recording medium to be recorded having an ink receiving layer containing a phosphor, then irradiating the recording medium to be recorded on which the test pattern is recorded with ultraviolet rays, and detecting fluorescence emitted from the phosphor".

However, the method for detecting a test pattern disclosed in JP 2006-110804 A is effective only when a special recording medium having an ink receiving layer containing a phosphor is used. This method cannot be applied to a case where a recording medium not containing a phosphor is used. Therefore, there is a demand for a technique capable of detecting a test chart recorded on a recording medium by ink having poor visibility irrespective of characteristics of the recording medium.

SUMMARY

An object of the present invention is to provide an inkjet recording device and a test chart detection method capable of improving detection accuracy of a test chart recorded on a recording medium by ink having poor visibility irrespective of characteristics of the recording medium.

To achieve the abovementioned object, according to an aspect of the present invention, an inkjet recording device reflecting one aspect of the present invention comprises: an inkjet head that forms an image on a recording medium by ejecting ink containing a phosphor onto the recording medium; an ultraviolet light source that irradiates the image formed on the recording medium with ultraviolet rays; and an imager that detects fluorescence emitted by the image by the irradiation of the ultraviolet rays.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, an inkjet recording device and a test chart detection method according to one or more embodiments of the present invention will be described with reference to the drawings. However, the scope of the invention is not limited to the disclosed embodiments. In the respective figures described below, common members are denoted by the same symbol. Descriptions will be given in the following order.

1. First Embodiment (example in which two image readers are included)

1-1. Overall Configuration of Inkjet Recording Device 1-2. Configuration of Control System of Inkjet Recording Device 1-3. Test Chart Detection Method 2. Second Embodiment (example in which one image reader is included)

2-1. Configuration of Image Reader 2-2. Test Chart Detection Method

1. First Embodiment (Example in which Two Image Readers are Included)

1-1. Overall Configuration of Inkjet Recording Device

Figure 1:
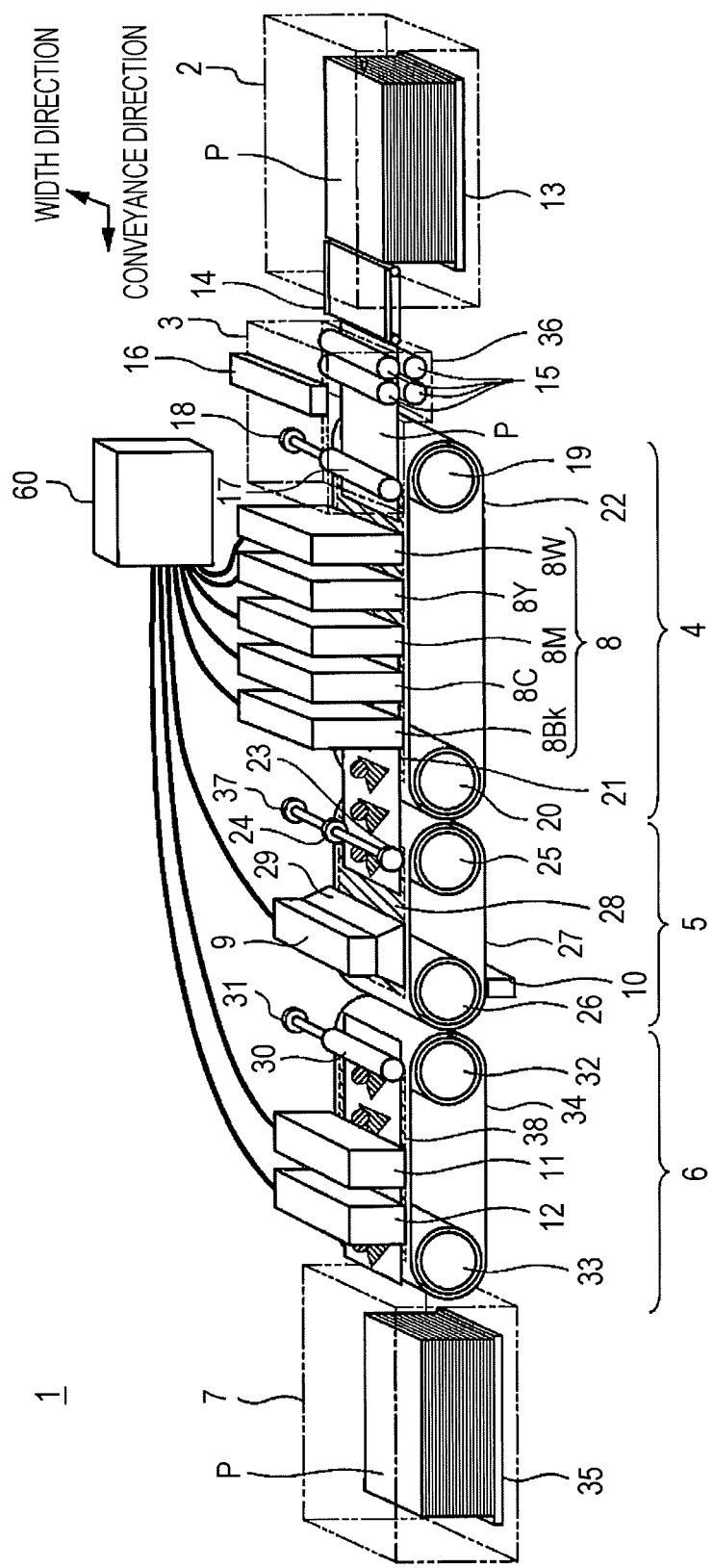
FIG. 1 is an overall configuration diagram of an inkjet recording device according to a first embodiment of the present invention.

FIG. 1 is an overall configuration diagram of an inkjet recording device 1 according to a first embodiment of the present invention (hereinafter referred to as the present embodiment). As illustrated in FIG. 1, the inkjet recording device 1 includes a medium supplier 2, a medium heater 3 (temperature adjuster), a first conveyor 4, a recorder 8, a second conveyor 5, a fixer 9, a cooler 10, and a third conveyor 6. The inkjet recording device 1 further includes a first image reader 11, a second image reader 12, a medium ejector 7, and a controller 60.

[Medium Supplier]

The medium supplier 2 has a medium stacker 13 and a positioner 14. A flat plate (tray) is provided in the medium stacker 13, and a plurality of recording media P, which are papers of a set size in this case although not specifically limited thereto, is stacked therein. In the medium stacker 13, the uppermost recording medium P is sequentially sent to the positioner 14 substantially horizontally with the plate moving up and down depending on the stacking amount of the recording media P.

The positioner 14 includes a guide member or the like for positioning a recording medium P, particularly to a predetermined position in the width direction perpendicular to a conveyance direction of the recording medium P and feeds the recording medium P to the first conveyor 4 at an appropriate position and timing.

[Medium Heater]

In the medium heater 3, a recording medium P is sandwiched by a plurality of heating rollers 15 from both sides. The medium heater 3 heats up the recording medium P while conveying the recording medium P by turning motion. A medium heater (not illustrated) is included in the plurality of heating rollers 15, and the surface of the heating rollers 15 is heated and transmits the heat to the recording medium P, thereby heating the recording medium P. As the medium heater, for example, an electric heating sheet or the like which generates Joule heat by a current is used.

In addition, a heating chamber 36 is provided over the heating rollers 15 to a part of the first conveyor 4. The temperature of the heating chamber 36 is kept constant by an air heater 16, thereby mitigating temperature unevenness of the recording medium P heated by the heating rollers 15. In this manner, the recording medium P is allowed to have a substantially uniform temperature. As the air heater 16, for example, an infrared heater for emitting infrared rays and the like can be used.

The heating chamber 36 is provided so as to encircle a part of an upstream part in the conveyance direction of a section on which the recording medium P is placed on a placement surface of a conveyance belt 22 included in the first conveyor 4 which will be described later. The recording medium P is placed on the conveyance belt 22 inside the heating chamber 36.

[First Conveyor]

The first conveyor 4 includes a driving roller 20, a driven roller 19, the endless conveyance belt 22, a first adsorber 21, a pressing roller 17, and a first pressing motor 18.

Here, the endless conveyance belt 22 is a steel belt, for example. The conveyance belt 22 is bridged over the driving roller 20 and the driven roller 19 to perform rotating motion (moving motion). The recording medium P is placed on the placement surface in a section in which the outer circumferential surface (placement surface for the recording medium P) of the conveyance belt 22 faces upward and moves horizontally, and the recording medium P is conveyed as the conveyance belt 22 rotates. In this section, the recording medium P and the conveyance belt 22 face a surface (ink ejection surface) from which ink is ejected from nozzles of respective head units 8Y, 8M, 8C, and 8K of the recorder 8. The conveyance belt 22 has a structure in which a number of openings penetrate through both surfaces in a predetermined pattern such that the air can pass from the placement surface side to the surface opposite to the placement surface.

The pressing roller 17 prevents (suppresses) the recording medium P from being raised from the placement surface when the recording medium P is placed on the placement surface of the conveyance belt 22 in accordance with the motion of the first pressing motor 18 and allows the recording medium P to move in the conveyance direction while keeping the recording medium P in close contact with the placement surface. The pressing roller 17 presses the recording medium P to such an extent that the recording medium P is not compressed, and the rotation speed is controlled such that the moving speed of the surface of the pressing roller 17 is the same as the moving speed of the conveyance belt 22. Note that the pressing roller 17 may not be driven to rotate and may rotate merely in accordance with the movement of the recording medium P.

The first adsorber 21 allows the recording medium P to be adsorbed on the placement surface of the conveyance belt 22. For example, the first adsorber 121 has a support plate (not illustrated) for supporting the conveyance belt 22 forming the placement surface on the side opposite to the placement surface and a suction fan (not illustrated). The suction fan is provided in the interior surrounded by the inner circumferential surface of the conveyance belt 22. In addition, a large number of through holes are included in the support plate such that the air sucked from the placement surface side of the conveyance belt 22 to the suction fan by the operation of the suction fan can pass therethrough. Alternatively, a porous body can be used instead of the support plate having through holes formed artificially.

[Recorder]

The recorder 8 is provided on the downstream side of the medium heater 3 in the conveyance direction of the recording medium P. The recorder 8 has head units 8W, 8Y, 8M, 8C, and 8Bk provided individually for the colors of white (W), yellow (Y), magenta (M), cyan (C), and black (Bk). The head units 8W, 8Y, 8M, 8C, and 8Bk are arranged in the order of the head units 8W, 8Y, 8M, 8C, and 8Bk from the upstream side in the conveyance direction of the recording medium P, for example.

Figure 2:
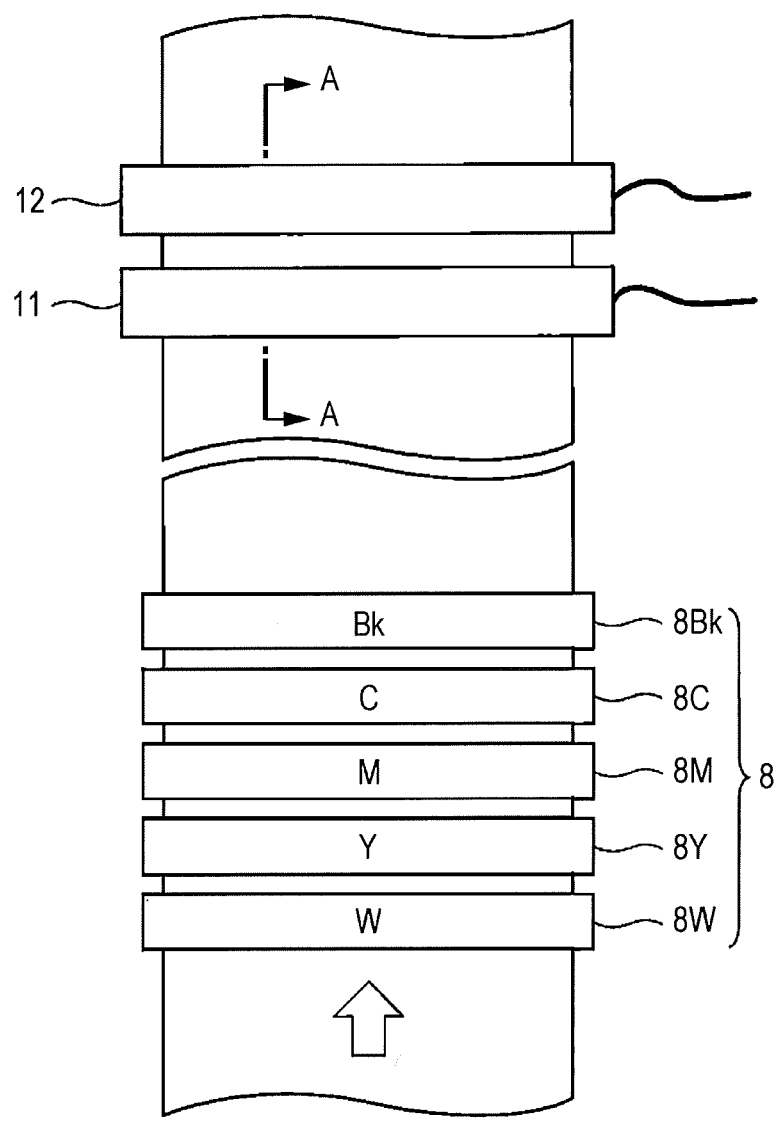
FIG. 2 is a diagram of a main part of the inkjet recording device according to the first embodiment of the present invention when viewed from above.

FIG. 2 is a diagram of the main part of the inkjet recording device 1 according to the present embodiment when viewed from above. In FIG. 2, the recorder 8, the first image reader 11, and the second image reader 12 in the inkjet recording device 1 are extracted and illustrated. As illustrated in FIG. 2, each of the head units 8W, 8Y, 8M, 8C, and 8Bk has a length (width) that covers the entire recording medium P in a direction perpendicular to the conveyance direction of the recording medium P (width direction of the recording medium P). That is, the inkjet recording device 1 is a one-pass type inkjet recording device of a line head type.

Figure 3:
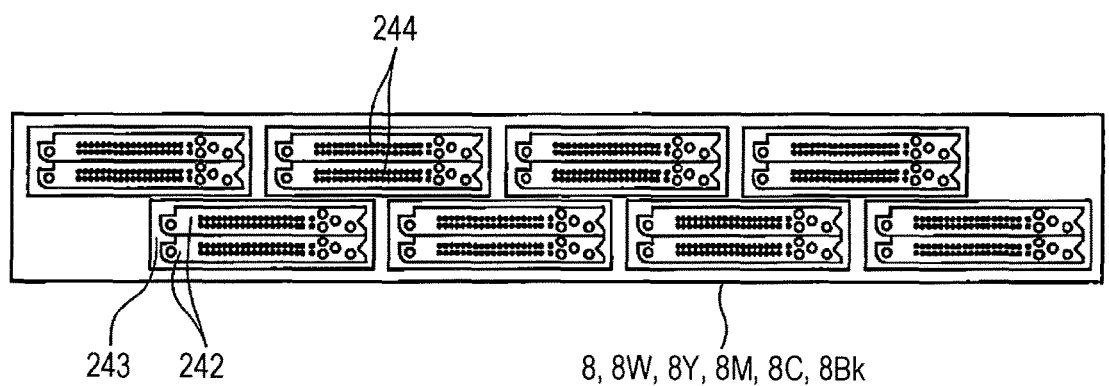
FIG. 3 is a plan view of one of head units included in a recorder when viewed from a recording medium side.

FIG. 3 is a plan view of one of the head units 8W, 8Y, 8M, 8C, and 8Bk when viewed from the recording medium P side. As illustrated in FIG. 3, each of the head units 8W, 8Y, 8M, 8C, and 8Bk has a plurality of (16 in this embodiment) inkjet heads 242. Two inkjet heads 242 make a pair to form one inkjet module 243. Therefore, each of the head units 8W, 8Y, 8M, 8C, and 8Bk of the present embodiment includes eight inkjet modules 243.

The eight inkjet modules 243 are arranged in two rows along the conveyance direction of the recording medium P. Four inkjet modules 243 of one row are arranged in alignment along the direction (width direction) orthogonal to the conveyance direction of the recording medium P. Of the eight inkjet modules 243, two rows of inkjet modules 243 are arranged in a zigzag pattern along the conveyance direction of the recording medium P.

Note that the number and arrangement of the inkjet modules 243 in each of the head units 8W, 8Y, 8M, 8C, and 8Bk are not limited to those described above, and six or ten or more inkjet modules 243 may be arranged. Alternatively, a single head unit in which multiple nozzles are arranged in one unit may be adopted.

A plurality of openings included on a surface of an inkjet head 242 which is included in each of the head units 8W, 8Y, 8M, 8C, and 8Bk and is facing the outer circumferential surface of the conveyance belt 22 serves as nozzles 244. From a plurality of nozzles 244 of inkjet heads 242 in head units 8W, 8Y, 8M, 8C, and 8Bk, ink of a color corresponding to the head units 8W, 8Y, 8M, 8C, and 8Bk, respectively, is ejected. Ink ejected from the nozzles 244 is impacted on a surface (recording surface) of the recording medium P facing the recorder 8. In this embodiment, inks of respective colors of W, Y, M, C, and Bk are sequentially ejected from the head units 8W, 8Y, 8M, 8C, and 8Bk onto the recording medium P, thereby forming a desired image on the recording medium P.

Ink used in the inkjet recording device 1 of this embodiment is, for example, an ultraviolet (UV) curing type ink. The UV curing type ink undergoes a phase change between a gel state and a liquid (sol) state depending on the temperature when not irradiated with UV. In the present embodiment, known ultraviolet curing type inks of yellow, magenta, cyan, and black can be used.

White ink supplied to the head unit 8W of this embodiment is a UV curing type ink to which a phosphor has been added. The phosphor contained in the white ink may be any substance as long as the substance can emit light having a wavelength in the visible region of 450 nm or more when irradiated with light having a wavelength in the ultraviolet range of 390 nm or less, for example. As such a phosphor, for example, inorganic phosphors such as $ZnSiO_4$ and $MgWO_4$ or organic phosphors such as coumarin derivatives, stilbene derivatives, pyrene derivatives, oxazole derivatives, thiazole derivatives, imidazole derivatives, imidazolone derivatives, pyrazoline derivatives may be used.

As the phosphor to be added to the white ink in the present embodiment, it is also possible to use a fluorescent whitening agent which is generally used for making an object appear whiter. Examples of usable fluorescent whitening agents in this embodiment include those commercially available under the trade names of Uvitex (registered trademark) series and Tinopal (registered trademark) series from Ciba Specialty Chemicals, Kayacoll (registered trademark) series from Nippon Soda Co., Ltd., Whitex (registered trademark) series from Sumitomo Chemical Industry Company Limited, Kayaphor (registered trademark) series from Nippon Kayaku Co., Ltd., and Blankophor (registered trademark) series from Bayer AG. In the case where these fluorescent whitening agents are water-soluble dyes, they may be anionic or cationic depending on the type of a water-soluble substituent, and either one may be used. Alternatively, oil-soluble dyes may be dispersed and used.

[Second Conveyor]

As illustrated in FIG. 1, the second conveyor 5 receives the recording medium P conveyed by the first conveyor 4 and conveys the recording medium P while allowing the recording medium P to pass through an irradiation section of ultraviolet rays by the fixer 9. The second conveyor 5 includes a driving roller 26, a driven roller 25, an endless conveyance belt 27, a second adsorber 28, pressing rollers 23 and 24, a second pressing motor 37, and a cooler 10. Since a configuration of the second conveyor 5 is similar to that of the first conveyor 4 except that the two pressing rollers 23 and 24 are provided instead of the pressing roller 17, detailed descriptions of the second conveyor 5 will be omitted.

The pressing rollers 23 and 24 press both ends of the recording medium P in the width direction. The ink ejected by the recorder 8 on the first conveyor 4 and is impacted onto the recording medium P is not fixed on the recording medium P at the time when the recording medium P is delivered to the second conveyor 5. Therefore, the pressing rollers 23 and 24 press only the margin parts at both ends in the width direction so as not to disturb the impacted ink by pressing the impacted parts of the ink in the above state. The positions of the pressing rollers 23 and 24 in the width direction can be changed by a user and/or under the control of the controller 60.

The height of a section of the outer circumferential surface (placement surface) of the conveyance belt 27 on which the recording medium P is placed and is moved in parallel is set to be equivalent to the height of the section of the outer circumferential surface (placement surface) of the conveyance belt 22 on which the recording medium P is placed and is moved in parallel. In this manner, with the recording medium P delivered directly from the conveyance belt 22 to the conveyance belt 27, the recording medium P is moved and conveyed on a single plane without the height thereof being changed.

Here, the term "equivalent" is not limited to the case of being exactly equal, but it is sufficient to have an accuracy of being approximately equal by visual inspection in an assembly setting of normal mechanical devices, for example being equal within a range of about 1 cm or less, more preferably about 1 mm or less.

[Fixer]

The fixer 9 fixes, to the recording medium P, the ink impacted on the recording medium P on the placement surface of the conveyance belt 27. The fixer 9 includes an irradiator (not illustrated) of ultraviolet rays and irradiates the ultraviolet curing ink on the recording medium P with ultraviolet rays.

It is preferable that ultraviolet rays emitted from the fixer 9 irradiate the recording medium P without including significant unevenness (variations in intensity) in the section where the recording medium P is placed on the placement surface of the conveyance belt 27. Meanwhile, a light shielding plate 29 is provided so as to surround the irradiation range of ultraviolet rays by the fixer 9 in order to reduce the intensity of ultraviolet rays leaking outside the section. The light shielding plate 29 is formed of, for example, a plate-shaped member extending toward the conveyance belt from the position where the irradiator in the fixer 9 is provided and having such a length that the light shielding plate 29 does not contact the conveyance belt.

Furthermore, depending on the type of ink, the fixer 9 and a region including the irradiation range of ultraviolet rays may be accommodated in a housing, and by filling the housing with a specific gas such as nitrogen gas, the fixing effect in the fixer 9 can be improved. Alternatively, even in the case where a housing is not provided, similar effects can be obtained by filling the region surrounded by the light shielding plate 29 with a specific gas. In the case where a predetermined region including the fixer 9 and the irradiation range of ultraviolet rays is filled with a specific gas, in order to prevent heat from remaining in the space filled with the gas, it is preferable to perform circulation cooling of the gas, cooling of the housing, or other cooling operations as appropriate.

[Cooler]

The cooler 10 cools the heat generated in association with the fixing of the ink on the recording medium P by the operation of the fixer 9 and the conveyance belt 27 that has been heated in association with the heat generation of the fixer 9 itself. The cooler 10 has a cooling fan, for example, and air-cools the conveyance belt 27 by the operation of the cooling fan. The cooler 10 is provided to face the placement surface in a section where the recording medium P is not placed on the placement surface of the conveyance belt 27.

Note that the cooler 10 is provided as a component for cooling the conveyance belt 27 here; however, a component that cools the irradiator of ultraviolet rays itself in the fixer 9 may be included such that overheating of the irradiator at the time of recording images for a long time can be prevented.

[Third Conveyor]

The third conveyor 6 receives the recording medium P conveyed by the second conveyor 5 and conveys the recording medium P while allowing the recording medium P to pass inside reading ranges of the first image reader 11 and the second image reader 12. The third conveyor 6 includes a driving roller 33, a driven roller 32, an endless conveyance belt 34, a third adsorber 38, a pressing roller 30, and a third pressing motor 31. Configurations of the driving roller 33, the driven roller 32, the conveyance belt 34, the third adsorber 38, the pressing roller 30, and the third pressing motor 31 are the same as those of the driving roller 20, the driven roller 19, the conveyance belt 22, the first adsorber 21, the pressing roller 17, and the first pressing motor 18, respectively, and thus detailed descriptions thereof will be omitted.

The height of a section of the outer circumferential surface (placement surface) of the conveyance belt 34 on which the recording medium P is placed and is moved in parallel is set to be equivalent to the height of the section of the outer circumferential surface (placement surface) of the conveyance belt 27 on which the recording medium P is placed. The recording medium P is directly handed over on the same plane from the placement surface of the conveyance belt 27 to the placement surface of the conveyance belt 34. That is, the recording medium P is moved and handed over on the single plane after having been placed on the conveyance belt 22 in the first conveyor 4 until the recording medium P is removed from the conveyance belt 34 in the third conveyor 6.

[First Image Reader, Second Image Reader]

The first image reader 11 and the second image reader 12 are provided on a downstream side of the fixer 9 in the conveyance direction of the recording medium P and read the image surface of the recording medium P conveyed by the conveyance belt 34 as illustrated in FIG. 1. Moreover, in the present embodiment, the first image reader 11 and the second image reader 12 are arranged in the order mentioned from the fixer 9 side in the conveyance direction of the recording medium P.

Figure 4A:
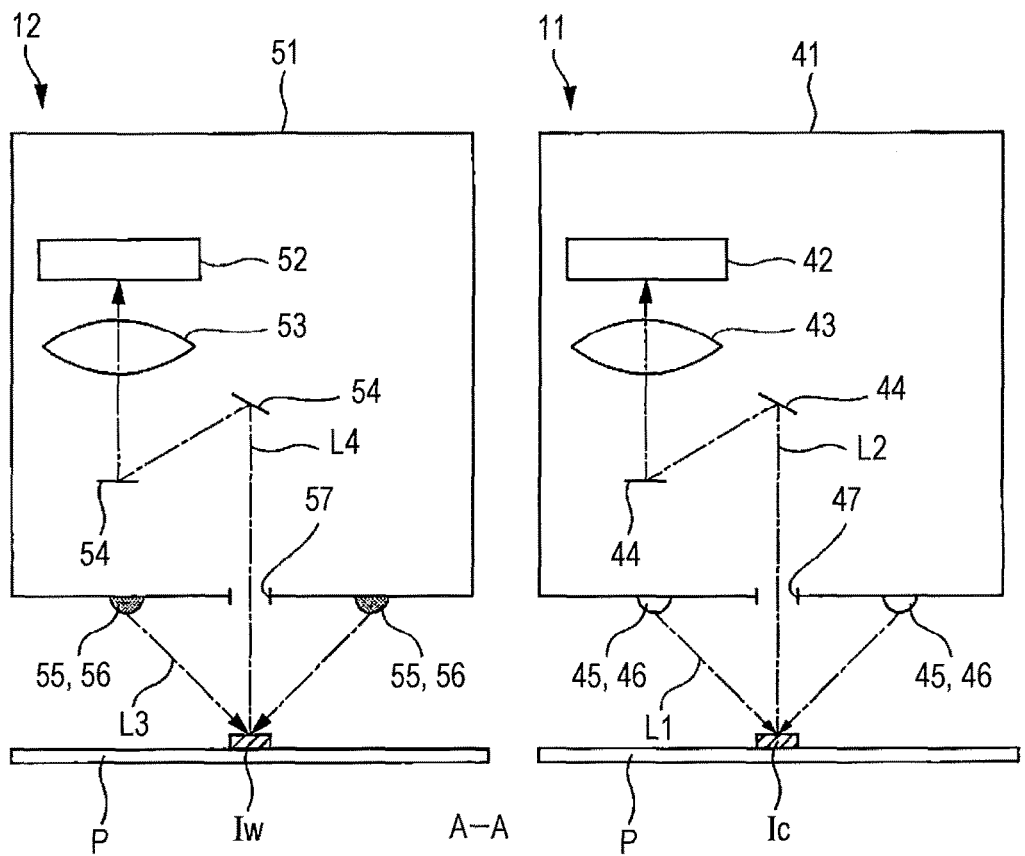
FIG. 4A is a cross-sectional configuration diagram along line A-A in FIG. 2.
Figure 4B:
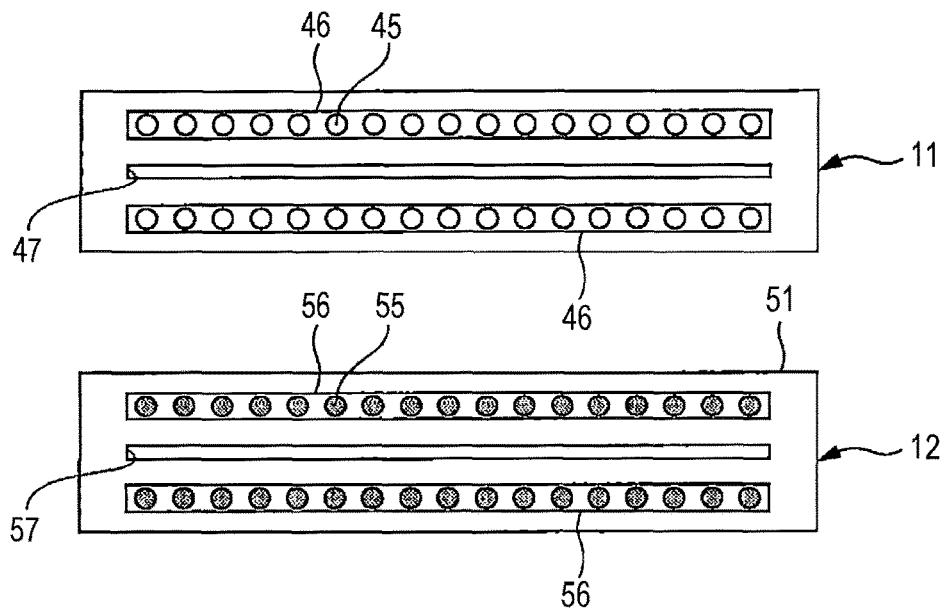
FIG. 4B is a plan view of a first image reader and a second image reader when viewed from the recording medium side.

FIG. 4A is a cross-sectional configuration diagram along line A-A in FIG. 2, the diagram illustrating internal configurations of the first image reader 11 and the second image reader 12. FIG. 4B is a plan view of the first image reader 11 and the second image reader 12 when viewed from a surface facing the recording medium P.

The first image reader 11 includes first irradiators 46 that irradiate the recording medium P conveyed on the placement surface of the conveyance belt 34 with white light, a first imager 42 (corresponding to a white light side imager) that detects reflection light from the recording medium P, and a first housing 41 provided with the first irradiators 46 and the first imager 42.

The first housing 41 is formed of a box-shaped member longer than the width direction orthogonal to the conveyance direction of the recording medium P. On a surface of the first housing 41 that faces the placement surface of the conveyance belt 34 for the recording medium P, a first opening 47 of a line shape corresponding to the width direction orthogonal to the conveyance direction of the recording medium P is included. The width of the first opening 47 in the width direction orthogonal to the conveyance direction of the recording medium P is set to be equivalent to or slightly wider than the maximum width of image recording possible in the recorder 8. Meanwhile, the width of the first opening 47 in the direction along the conveyance direction of the recording medium P is set to allow reflection light L2 from the recording medium P to enter.

The first irradiator 46 includes a plurality of white light sources 45 including white light emitting diodes (LEDs), for example. The first irradiators 46 are provided in two rows so as to interpose the first opening 47 of the first housing 41 therebetween. In a first irradiator 46, a plurality of white LEDs is arranged in a row along the width direction orthogonal to the conveyance direction of the recording medium P. The two rows of the first irradiators 46 configured in this manner are set such that the emitted white light L1 is incident on the image surface of the recording medium P positioned immediately below the first opening 47 at an incident angle of 45°, for example. In the present embodiment, the first irradiators 46 are provided in two rows; however, the present invention is not limited thereto.

The first imager 42 is arranged inside the first housing 41 and includes, for example, a charge coupled device (CCD) sensor or a complementary metal oxide semiconductor (CMOS) sensor. The first imager 42 includes a line sensor having sensitivity to light having a wavelength in the visible light region. The first imager 42 is arranged to enable capturing a range equivalent to or slightly wider than the maximum width of an image that can be recorded in the recorder 8. Note that the resolution of the line sensor applied to the first imager 42 is generally rougher than the nozzle pitch.

In addition, a plurality of reflecting mirrors 44 (two in FIG. 4A) and a desired lens system 43 are arranged in an optical path, to the first imager 42, of the reflection light L2 reflected by the image surface of the recording medium P and entering the first housing 41.

Under the control of the controller 60, the first irradiator 46 emits the white light L1 when an image Ic formed on the recording medium P passes immediately below the first opening 47. Then, the first imager 42 provided inside the first housing 41 detects the reflection light L2 reflected by the image surface. As a result, the first image reader 11 can capture a one-dimensional image of the image formed on the recording medium P. Furthermore, the first image reader 11 can acquire a two-dimensional image by repeating imaging at intervals corresponding to the conveyance speed of the recording medium P.

In the present embodiment, under the control of the controller 60, the image Ic formed by inks of yellow, magenta, cyan, or black is read by the first image reader 11.

The second image reader 12 includes a second irradiator 56, a second imager (corresponds to the imager) 52, and a second housing 51 provided with the second irradiator 56 and the second imager 52.

The second image reader 12 is different from the first image reader 11 only in the configuration of the second irradiator 56. The configurations of the second housing 51, a second opening 57, the second imager 52, a plurality of reflecting mirrors 54, and a lens system 53 in the second image reader 12 are similar to those of the first housing 41, the first opening 47, the first imager 42, the plurality of reflecting mirrors 44, and the lens system 43 in the first image reader 11, respectively. Therefore, redundant descriptions thereof will be omitted.

The second irradiator 56 includes a plurality of ultraviolet light sources 55 including LEDs that emit ultraviolet rays. The second irradiators 56 are provided in two rows so as to interpose the second opening 57 of the second housing 51 therebetween. In a second irradiator 56, a plurality of ultraviolet LEDs is arranged in a row along the width direction orthogonal to the conveyance direction of the recording medium P. The two rows of the second irradiators 56 configured in this manner are set such that emitted ultraviolet rays L3 are incident on the image surface of the recording medium P positioned immediately below the second opening 57 at an incident angle of 45°, for example.

In the present embodiment, the example where the second irradiators 56 include ultraviolet LEDs that emit ultraviolet rays; however, the second irradiator 56 is only required to emit ultraviolet rays of 360 nm or less, for example, and ultraviolet lasers or ultraviolet lamps such as low-pressure mercury lamps can be used instead of LEDs. The wavelength of ultraviolet rays in the second irradiator 56 may be any wavelength as long as the wavelength allows for emission of fluorescence when absorbed by the phosphor contained in the white ink and thus is determined as appropriate depending on the white ink used.

In the second image reader 12, under the control of the controller 60, the second irradiator 56 emits the ultraviolet rays L3 when an image Iw formed by the white ink among images formed on the recording medium P passes immediately below the second opening 57. In the present embodiment, the ink that forms the white image Iw contains a phosphor. Therefore, the ultraviolet rays L3 emitted to the image Iw formed by the white ink are absorbed by the image surface and emits fluorescence (excitation light) L4 of about 450 nm, for example. With the fluorescence L4 in the visible light region entering the second imager 52, the second imager 52 can detect the image Iw formed by the white ink as light having a wavelength in the visible light region.

Also in the present embodiment, the second image reader 12 can capture a one-dimensional image of the image formed on the recording medium P. Furthermore, the second image reader 12 can acquire a two-dimensional image by repeating imaging at intervals corresponding to the conveyance speed of the recording medium P.

Meanwhile, in the case where an image is formed by the white ink on a white recording medium P and the image is irradiated with white light, there is no big difference in the intensity of reflection light between a part where the image is formed and a part where the image is not formed. Therefore, in a case where an image is formed by the white ink on a white recording medium P, the visibility is poor, and the first image reader 11 cannot read an accurate image. As a result, a test chart of the white ink cannot be read accurately.

On the other hand, in the present embodiment, an image formed by the white ink is irradiated with the ultraviolet rays L3 in the second image reader 12. Thus, light having a wavelength converted into the visible light region by the effect of the phosphor can be detected. As a result, even when an image is formed by the white ink on a white recording medium P, visibility of the image formed by the white ink can be improved by emission of the ultraviolet rays L3. Therefore, in the second imager 52, it is possible to more accurately read the test chart of the white ink.

[Medium Ejector]

The medium ejector 7 holds the recording medium P conveyed by the third conveyor 6 and placed therein. The medium ejector 7 includes an ejecting tray 35 (plate), and recording media P on which image recording has been completed are sequentially placed in the ejecting tray 35. The ejecting tray 35 is set to be lower than a conveying surface of the third conveyor 6 such that the recording medium P can be sent out from the conveying surface and may be vertically movable depending on the amount of recording media P placed therein.

1-2. Configuration of Control System of Inkjet Recording Device

Figure 5:
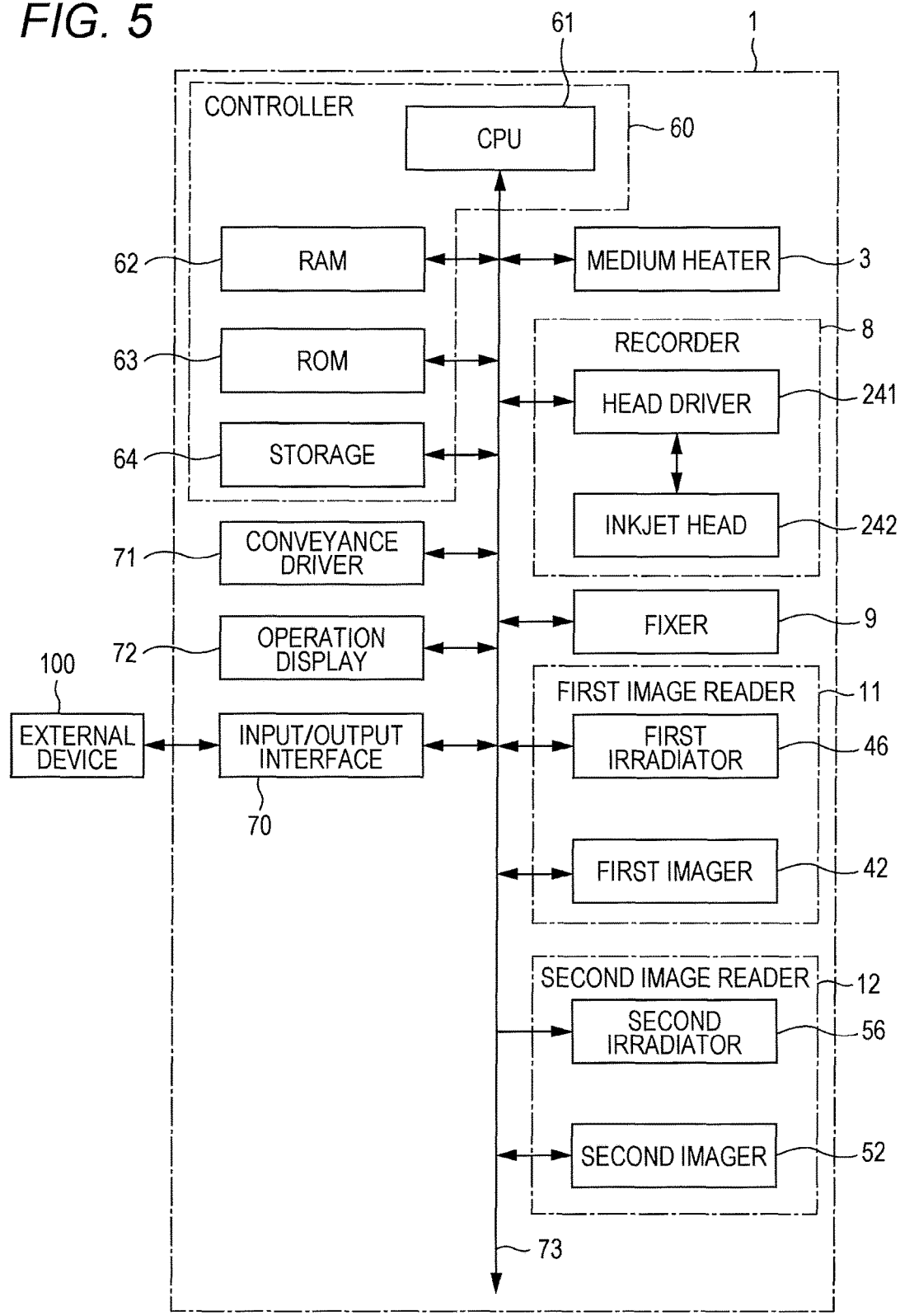
FIG. 5 is a block diagram illustrating a configuration of a control system of the inkjet recording device according to the first embodiment of the present invention.

FIG. 5 is a block diagram illustrating a configuration of a control system of the inkjet recording device 1 of the present embodiment. As illustrated in FIG. 5, the inkjet recording device 1 of the present embodiment includes the controller 60, an input/output interface 70, the medium heater 3, the recorder 8, the fixer 9, a conveyance driver 71, an operation display 72, the first image reader 11, and the second image reader 12.

The controller 60 includes, for example, a central processing unit (CPU) 61, a random access memory (RAM) 62 used as a work area of the CPU 61, and a read only memory (ROM) 63 for storing programs executed by the CPU 61. The controller 60 further has a storage 64 including a hard disk drive (HDD) or other devices as a mass storage device. In the storage 64, data for images read by the first image reader 11 and the second image reader 12, test charts for detecting ejection failures of the nozzles, and information for performing ejection failure inspecting operation of the nozzles are stored.

The CPU 61 of the controller 60 is connected to the RAM 62, the ROM 63, the storage 64, the input/output interface 70, the medium heater 3, the recorder 8, the fixer 9, the conveyance driver 71, the operation display 72, the first image reader 11, and the second image reader 12 via a system bus. The controller 60 controls the entire device.

Under the control of the controller 60, the conveyance driver 71 controls driving of each of the first conveyor 4, the second conveyor 5, and the third conveyor 6. The operation display 72 is a touch panel including an image display device such as a liquid crystal display (LCD) or an organic LED. The operation display 72 displays an instruction menu for a user, information related to the ejection detection operation of the nozzles, information related to acquired image data, or other information. The operation display 72 further includes a plurality of keys and serves as an inputter for accepting data input such as various instructions, characters, numerals, etc. by a user's key operation.

The input/output interface 70 is connected to an external device 100 such as a personal computer (PC) or a facsimile machine. The input/output interface 70 outputs received image data to the controller 60. The controller 60 performs image processing on the image data received from the input/output interface 70. The controller 60 further performs image processing such as shading correction, image density adjustment, or image compression on the received image data as necessary.

The recorder 8 receives the image data subjected to image processing by the controller 60 and forms a predetermined image on the recording medium P on the basis of the image data. Specifically, by driving the respective head drivers 241 of the head units 8W, 8Y, 8M, 8C, and 8Bk constituting the recorder 8, ink is ejected from each of the inkjet heads 242 to a predetermined position of the recording medium P.

Under the control of the controller 60, the first image reader 11 emits white light from the first irradiator 46 at a predetermined timing and detects reflection light thereof by the first imager 42. Furthermore, under the control of the controller 60, the second image reader 12 emits ultraviolet rays from the second irradiator 56 at a predetermined timing and captures reflection light thereof by the second imager 52. The controller 60 discriminates a nozzle in which ejection failure is occurring on the basis of the image data sent from the first image reader 11 and the second image reader 12.

1-3. Test Chart Detection Method

Next, a test chart detection method in the inkjet recording device 1 of the present embodiment will be described. In the present embodiment, under the control of the controller 60, a predetermined test chart is formed on a recording medium P for each of the head units 8W, 8Y, 8M, 8C, and 8Bk.

Under the control of the controller 60, the first image reader 11 irradiates a test chart of yellow, magenta, cyan, or black formed on the recording medium P with the white light L1 emitted from the first irradiator 46 and images the test chart by the first imager 42. As a result, in the first image reader 11, test chart image data formed by each of the inks of yellow, magenta, cyan, and black is acquired in the first imager 42. The image data of each of the test charts of yellow, magenta, cyan, and black acquired by the first imager 42 is sent to the controller 60. The controller 60 detects a nozzle with ejection failure in each of the head units 8Y, 8M, 8C, and 8Bk from the image data of the test charts.

Meanwhile in the second image reader 12, under the control of the controller 60, a white test chart formed on the recording medium P is irradiated with the ultraviolet rays L3 emitted from the second irradiator 56 and the test chart is imaged. In the present embodiment, since the phosphor is added to the white ink, the ultraviolet rays L3 emitted to the test chart formed by the white ink are absorbed by the white test chart and the fluorescence L4 in the visible light region is emitted. The fluorescence L4 is incident on the second imager 52. As a result, the second imager 52 can detect the test chart formed by the white ink as a test chart in a predetermined visible light region, for example, blue. Image data of the white test chart acquired by the second imager 52 is sent to the controller 60, and the controller 60 detects a nozzle with ejection failure in the head unit 8W from the image data of the test chart.

As described above, since the phosphor is added to the white ink in the present embodiment, the phosphor contained in the test chart absorbs the ultraviolet rays L3 when irradiated with the ultraviolet rays L3 and emits the fluorescence L4. On the other hand, the part where the test chart is not formed does not emit fluorescence. As a result, the second imager 52 can detect the test chart formed by the white ink as light in the visible light region.

In the present embodiment, the phosphor is added to the white ink and the test chart formed by the white ink is read; however, the present invention is not limited to this example. For example, transparent ink used for the purpose such as improving the light fastness or water resistance of an image or giving gloss to an image also has poor visibility. Thus, it is difficult to detect transparent ink by an inline sensor. Therefore, also in the case of using transparent ink, by adding the phosphor used in this embodiment, it is possible to improve the visibility of an image formed by transparent ink under ultraviolet irradiation and to achieve similar effects to those of the present embodiment.

That is, in the case of using ink having poor visibility on a recording medium P, by adding a phosphor to the ink and irradiating an image formed by the ink added with the phosphor with ultraviolet rays, the image can be detected by the imager as an image in the visible light region. As a result, an image of a test chart can be acquired more accurately even in the case of using ink having poor visibility on a recording medium, and thus detection accuracy of a nozzle with ejection failure can be improved.

Furthermore in the present embodiment, since the visibility at the time of irradiation with ultraviolet rays can be improved by addition of a phosphor to ink having poor visibility, an ejection failure of a nozzle can be detected irrespective of characteristics of recording media.

2. Second Embodiment (Example in which One Image Reader is Included)

2-1. Configuration of Image Reader

Figure 6:
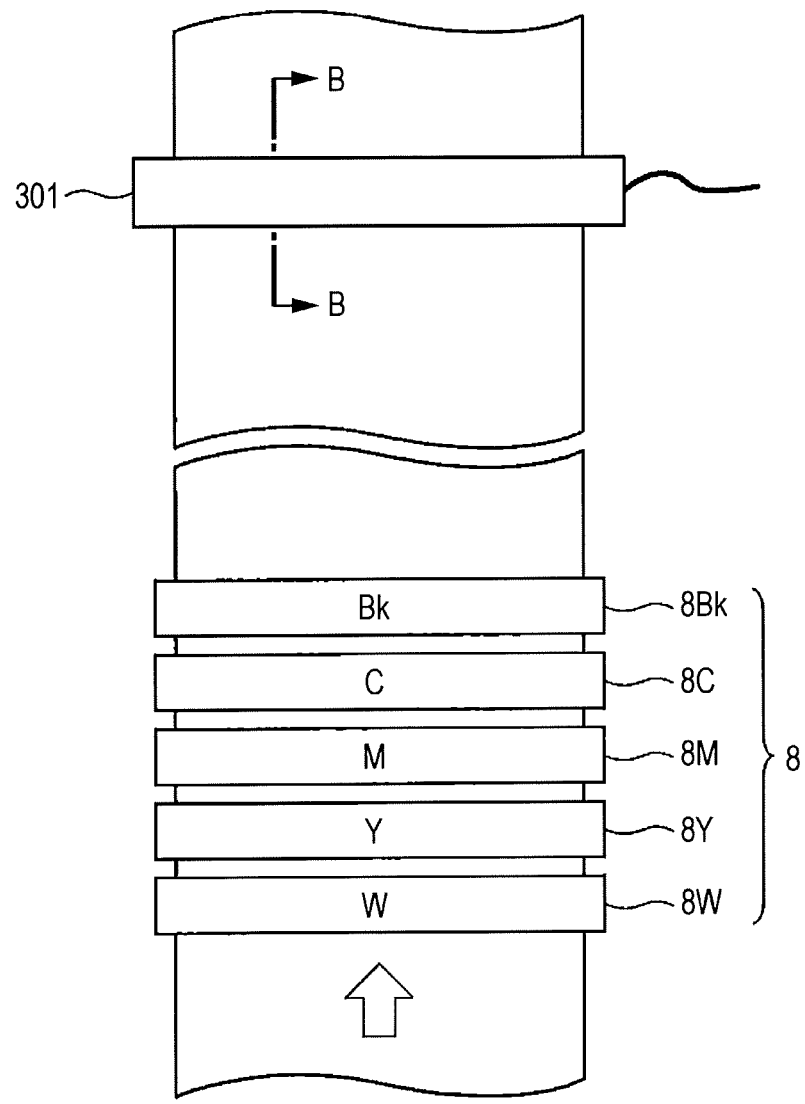
FIG. 6 is a configuration diagram illustrating a main part of an inkjet recording device according to a second embodiment of the present invention.

Next, an inkjet recording device 300 according to a second embodiment of the present invention will be described. FIG. 6 is a configuration diagram illustrating the main part of the inkjet recording device 300 according to the present embodiment. The inkjet recording device 300 of the present embodiment is an example in which only a configuration of an image reader 301 is different from that of the first embodiment. Therefore, descriptions of the overall configuration of the inkjet recording device 300 according to the present embodiment will be omitted. In FIG. 6, parts corresponding to those in FIG. 2 are denoted by the same symbols, and redundant explanations are omitted.

Also in the present embodiment, the image reader 301 is provided on a downstream side of a fixer in the conveyance direction of a recording medium P and reads a recording surface of the recording medium P conveyed by a conveyance belt 34 as illustrated in FIG. 6. In the present embodiment, the one image reader 301 reads a test chart formed by each of inks of white, yellow, magenta, cyan, and black.

Figure 7A:
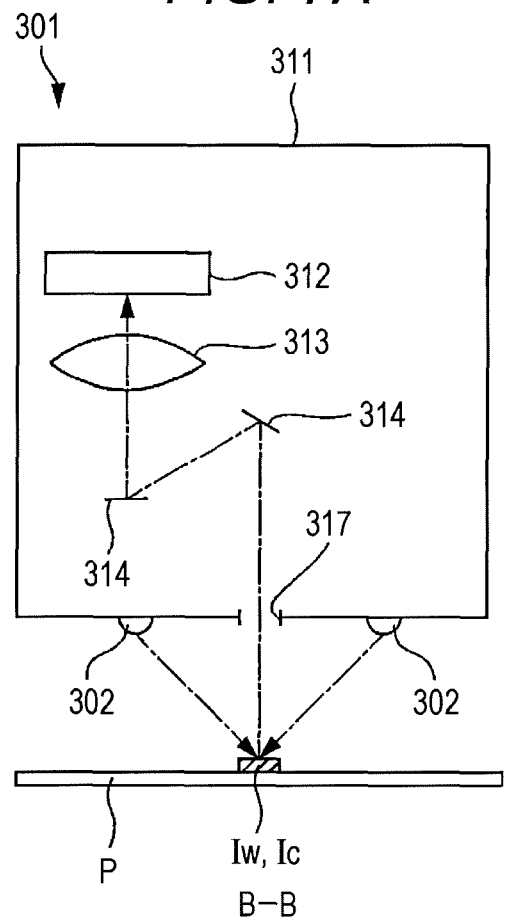
FIG. 7A is a cross-sectional configuration diagram along line B-B in FIG. 6.
Figure 7B:
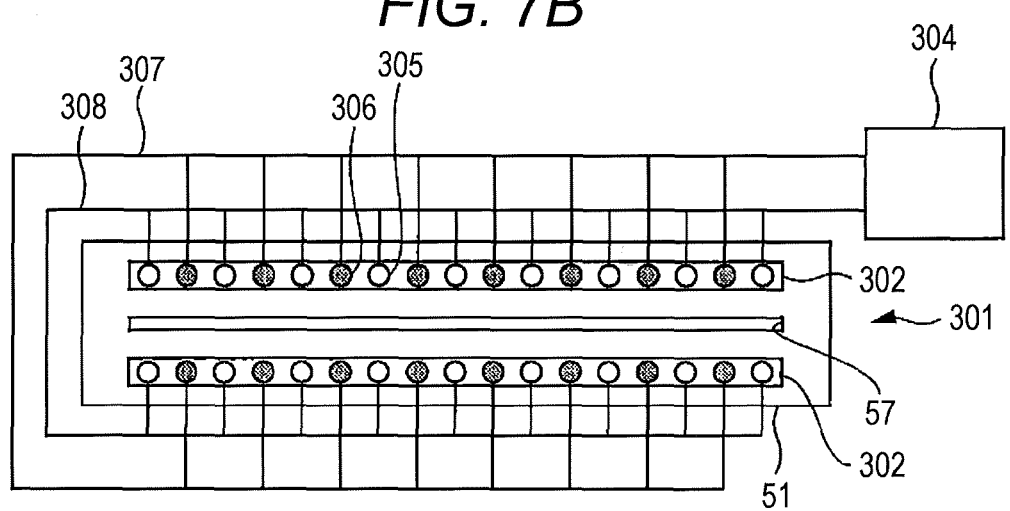
FIG. 7B is a plan view of an image reader when viewed from a recording medium side.

FIG. 7A is a cross-sectional configuration diagram along line B-B in FIG. 6, and FIG. 7B is a plan view of the image reader 301 when viewed from the recording medium P side partially illustrated by a block diagram.

As illustrated in FIG. 7A, the image reader 301 includes irradiators 302 capable of irradiating a recording medium P conveyed on a placement surface of the conveyance belt 34 with white light and ultraviolet rays, an imager 312 that images the recording medium P, and a housing 311 provided with the irradiators 302 and the imager 312. The image reader 301 further includes a light source switcher 304 that switches light sources in the irradiators 302.

The configuration of the irradiators 302 and the configuration of the light source switcher 304 of the image reader 301 are different from those of the first image reader 11.

Configurations of the housing 311, an opening 317, the imager 312, a plurality of reflecting mirrors 314, and a lens system 313 in the image reader 301 are similar to those of the first housing 41, the first opening 47, the first imager 42, the plurality of reflecting mirrors 44, and the lens system 43 in the first image reader 11, respectively. Therefore, redundant descriptions thereof will be omitted.

Each of the irradiators 302 includes a plurality of white light sources 305 including white LEDs and a plurality of ultraviolet light sources 306 including ultraviolet LEDs, which are alternately arranged. The irradiators 302 are provided in two rows so as to interpose the opening 317 of the housing 311 therebetween and are arranged along the width direction orthogonal to the conveyance direction of the recording medium P. That is, in the irradiator 302, the white light sources 305 and the ultraviolet light sources 306 are alternately arranged in a row along the extending direction of the opening 317 at positions interposing the opening 317. The two rows of the irradiators 302 configured in this manner are set such that emitted white light or ultraviolet rays are incident on the recording medium P positioned immediately below the opening 317 at an incident angle of 45°, for example.

The light source switcher 304 switches a connection state among first wiring 308 connected to the white light source 305 and second wiring 307 connected to the ultraviolet light sources 306 of the irradiators 302 and a power source (not illustrated). That is, in the light source switcher 304, white light is emitted from the white light sources 305 in the irradiators 302 when the first wiring 308 and the power source are connected, and ultraviolet rays are emitted from the ultraviolet light sources 306 in the irradiators 302 when the second wiring 307 and the power source are connected. That is, the light source switcher 304 switches between emission of the white light sources 305 and emission of the ultraviolet light sources 306.

Figure 8:
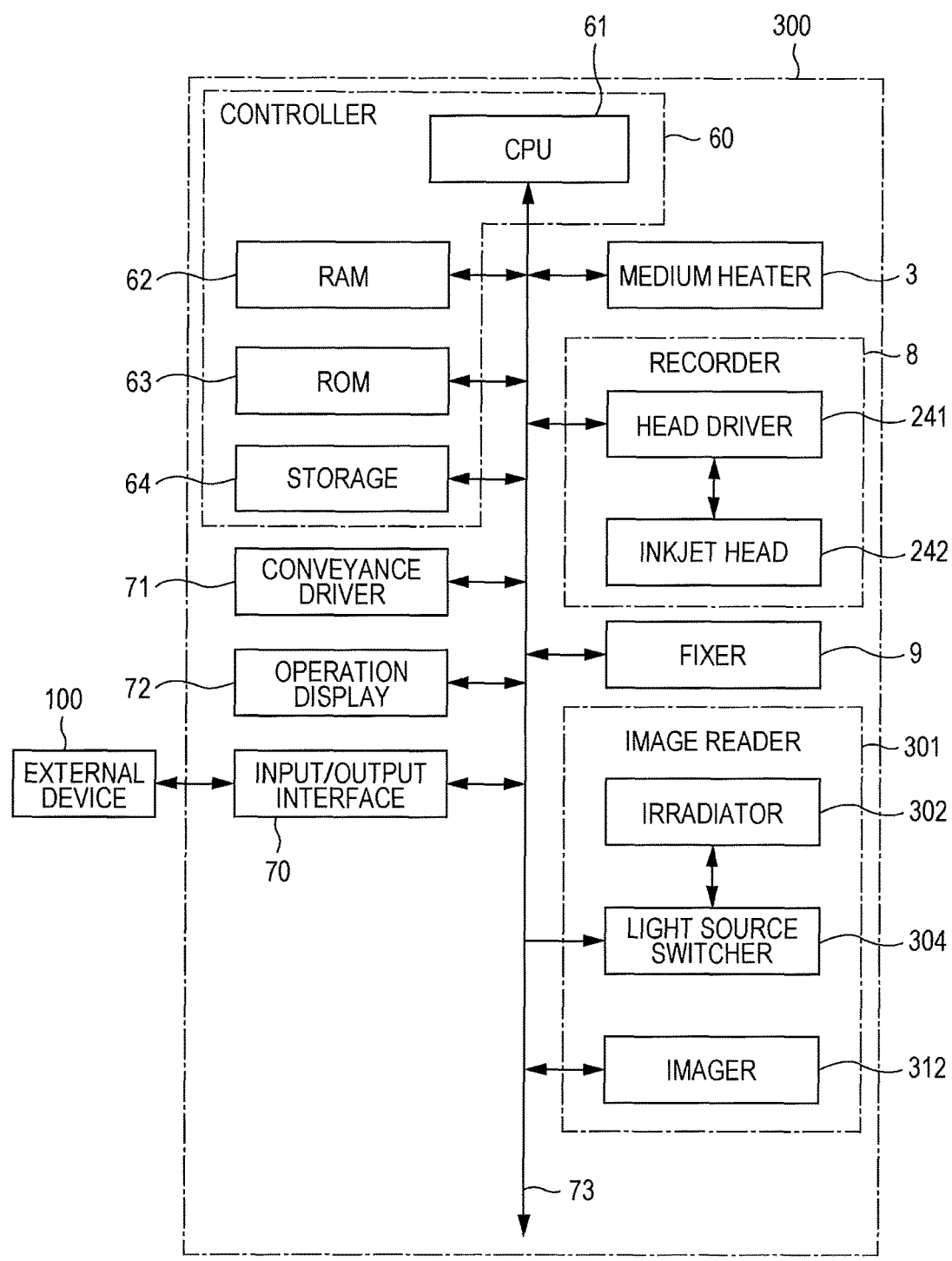
FIG. 8 is a block diagram illustrating a control system of the inkjet recording device according to the second embodiment of the present invention.

FIG. 8 is a block diagram illustrating a control system of the inkjet recording device 300 of the present embodiment. In FIG. 8, parts corresponding to those in FIG. 5 are denoted by the same symbols, and redundant explanations are omitted.

As illustrated in FIG. 8, in the image reader 301, under the control of the controller 60, the light source switcher 304 switches between the white light sources 305 and the ultraviolet light sources 306 in the irradiators 302. In the present embodiment, in the case where the image formed on the recording medium P is an image Ic formed by inks of yellow, magenta, cyan, or black, white light is emitted and reflection light thereof is acquired by the imager 312. On the other hand, in the case where the image formed on the recording medium P is the image Iw formed by the white ink, ultraviolet rays are emitted, and the imager 312 acquires fluorescence generated from the image Iw. In the imager 312, a one-dimensional image formed on the recording medium P can be imaged. Furthermore, the imager 312 can acquire a two-dimensional image by repeating imaging at intervals corresponding to the conveyance speed of the recording medium P.

2-2. Test Chart Detection Method

Next, a test chart detection method using the inkjet recording device 300 of the present embodiment will be described. In the present embodiment, under the control of the controller 60, a predetermined test chart is formed on a recording medium P for each of the head units 8W, 8Y, 8M, 8C, and 8Bk in the recorder 8.

In the image reader 301, under the control of the controller 60, the light source switcher 304 switches the irradiators 302 to the white light sources 305 at the timing when the test chart of yellow, magenta, cyan, or black formed on the recording medium P passes an irradiation position of the irradiators 302. Then, by detecting the reflection light of the white light emitted from the white light sources 305 by the imager 312, the test chart formed by each of the colors of yellow, magenta, cyan, and black is imaged.

As a result, in the image reader 301, test chart image data formed by each of the inks of yellow, magenta, cyan, and black is acquired in the imager 312. The image data of each of the test charts of yellow, magenta, cyan, and black acquired by the imager 312 is sent to the controller 60. The controller 60 detects a nozzle with ejection failure in each of the head units 8Y, 8M, 8C, and 8Bk from the image data of the test charts.

Meanwhile in the light source switcher 304, under the control of the controller 60, the irradiators 302 are switched to the ultraviolet light sources 306 at the timing when the white test chart formed on the recording medium P passes an irradiation position of the irradiators 302. Then, the test chart formed in white is irradiated with ultraviolet rays from the ultraviolet light sources 306. Since the phosphor is added to the white ink, the ultraviolet rays emitted to the test chart formed by the white ink is absorbed by the phosphor and emits fluorescence in the visible light region. Then, by detecting the fluorescence in the visible light region by the imager 312, the white test chart is imaged in the imager 312.

As a result, the imager 312 can image the test chart formed by the white ink as a test chart in a predetermined visible light region, for example, blue. Image data of the white test chart acquired by the imager 312 is sent to the controller 60, and the controller 60 detects a nozzle with ejection failure in the head unit 8W from the image data of the test chart.

As described above, in the present embodiment, by configuring the irradiators 302 of the image reader 301 to include the white light sources 305 and the ultraviolet light sources 306 and switching between the two at desired timings, it is possible to read test charts of all colors by one imager 312. This allows the device to be downsized.

Also in the present embodiment, white ink having poor visibility on a recording medium P contains a phosphor, and in the image reader 301, a test chart formed by the white ink is irradiated with ultraviolet rays, thereby imaging the reflection light. This allows the test chart formed by the white ink to be read by the imager 312 as light having a wavelength in the visible light region, and thus it is possible to accurately detect ejection failure of a nozzle.

Note that in the first and second embodiments, an image formed by yellow ink is detected by being irradiated with white light in the image reader, but there are also cases where an image formed by yellow ink also has low visibility. In this case, the image may be detected by adding a phosphor to the yellow ink and irradiating the image formed by the yellow ink with ultraviolet rays. Furthermore, a phosphor may be contained in inks of all colors used, and all images may be irradiated with ultraviolet rays to detect the images.

In addition, in the first and second embodiments described above, the inkjet head recording device having the line heads has been described as an example, but the configuration of the present invention can also be applied to a scanning type inkjet recording device. Furthermore, in the first and second embodiments, the example of using ultraviolet curing ink has been described, but the present invention is not limited thereto. For example, a thermosetting ink may be used.

In the first and second embodiments described above, the image reader is provided at a position apart from the recorder. Therefore, in the case of using ultraviolet curing ink, clogging of nozzles by the ultraviolet light sources included in the image reader can be prevented. In the first and second embodiments, the image reader is provided on the downstream side of the fixer in the conveyance direction of a recording medium, but the image reader may be provided between the recorder and the fixer. In this case, by providing the ultraviolet light sources at a position farther from the ink heads than the white light sources are, it is possible to prevent clogging of nozzles when ultraviolet curing ink is used.

The first and second embodiments described above have been described in detail in order to explain the present invention to facilitate understanding. The present embodiment is not necessarily limited to those having all of the configurations described above. For example, a part of a configuration of a certain embodiment can be replaced with a configuration of another embodiment, and a configuration of another embodiment can be added to a configuration of a certain embodiment. Furthermore, a part of a configuration of each of the embodiments can be added with, deleted of, or replaced with another configuration.

Although embodiments of the present invention have been described and illustrated in detail, the disclosed embodiments are made for purposes of illustration and example only and not limitation. The scope of the present invention should be interpreted by terms of the appended claims.

What is claimed is:

1. An inkjet recording device, comprising:
   an inkjet head that forms an image on a recording medium by ejecting an ultraviolet curing type ink containing a phosphor onto the recording medium;
   a fixer that fixes the ink impacted on the recording medium to the recording medium;
   an ultraviolet light source that irradiates the image formed on the recording medium with ultraviolet rays; and
   an imager that detects fluorescence emitted by the image by the irradiation of the ultraviolet rays,
   wherein the ultraviolet light source is at a position further downstream in a conveyance direction of the recording medium than the fixer.

2. The inkjet recording device according to claim 1,
   wherein the ink containing the phosphor is white or transparent.

3. The inkjet recording device according to claim 2, further comprising:
   a white light source that irradiates the image formed on the recording medium with white light; and
   a light source switcher that switches between emission of the ultraviolet light source and emission of the white light source.

4. The inkjet recording device according to claim 1, further comprising:
   a white light source that irradiates the image formed by the inkjet head on the recording medium with white light; and
   a white light-side imager that detects reflection light of the white light emitted to the image.

5. The inkjet recording device according to claim 4,
   wherein the ultraviolet light source is at a position further downstream in a conveyance direction of the recording medium than the white light source.

6. The inkjet recording device according to claim 1,
   wherein the fixer irradiates the ink with ultraviolet rays to cure the ink on the recording medium.

7. A test chart detection method, comprising:
   forming a test chart on a recording medium by ejecting an ultraviolet curing type ink containing a phosphor from an inkjet head onto the recording medium;
   fixing the ink impacted on the recording medium to the recording medium by a fixer;
   irradiating the test chart formed on the recording medium with ultraviolet rays from an ultraviolet light source; and
   in an imager, detecting fluorescence emitted by the test chart by the irradiation of the ultraviolet rays,
   wherein the ultraviolet light source is at a position further downstream in a conveyance direction of the recording medium than the fixer.

8. The test chart detection method according to claim 7,
   wherein the fixer fixes the ink impacted on the recording medium to the recording medium by irradiating the ink with ultraviolet rays to cure the ink on the recording medium.

* * * * *